United States Patent [19]

Shih et al.

[11] Patent Number: 5,686,067
[45] Date of Patent: Nov. 11, 1997

[54] LOW VOC HAIR SPRAY COMPOSITIONS

[75] Inventors: Jenn S. Shih, Paramus; Colleen M. Rocafort, Lake Hiawatha; Robert B. Login, Oakland, all of N.J.

[73] Assignee: ISP Investments Inc., Wilmington, Del.

[21] Appl. No.: 539,474

[22] Filed: Oct. 5, 1995

Related U.S. Application Data

[63] Continuation of Ser. No. 368,819, Jan. 5, 1995, abandoned.

[51] Int. Cl.⁶ .............................. A61K 7/11; A61K 7/06
[52] U.S. Cl. ........................ 424/70.15; 424/70.16; 424/DIG. 2; 424/47
[58] Field of Search ................... 424/70.11, 70.15, 424/70.17, 47, DIG. 2

[56] References Cited

U.S. PATENT DOCUMENTS 5,015,708  5/1991  Shih .......................... 526/264
5,326,555  7/1994  Handy ....................... 424/70.15

*Primary Examiner*—Salle M. Gahdner
*Attorney, Agent, or Firm*—Walter Katz; Marilyn J. Maue; Joshua J. Ward

[57] ABSTRACT

A low VOC (volatile organic compounds) hair spray composition having a combination of desirable user performance characteristics is described herein. The hair fixative resin in the composition is a terpolymer of 40–75% by weight of a vinyl lactam, preferably vinyl pyrrolidone, 15–40% of a polymerizable carboxylic acid, preferably acrylic acid or methacrylic acid, and 5–25% of a hydrophobic monomer, preferably a long chain alkyl ($C_8$–$C_{24}$) acrylate, methacrylate, acrylamide or methacrylamide. The terpolymer has a K-value of 30–55, preferably 40–50, which provides compositions having good sprayability in both pump and aerosol form, and small, fine spray particles.

7 Claims, No Drawings

LOW VOC HAIR SPRAY COMPOSITIONS

This is a continuation of application Ser. No. 08/368,819, filed Jan. 5, 1995, now abandoned.

BACKGROUND OF THE INVENTION

1. Field of the Invention

This invention relates to hair spray compositions, and, more particularly, to low VOC hair spray compositions containing a terpolymer of a vinyl lactam, a polymerizable carboxylic acid and a hydrophobic monomer, within a predetermined weight ratio, and with a K-value of 30–55, which provides desirable spray patterns and user hair care performance characteristics.

2. Description of the Prior Art

Recent legislation in California and other states have or will mandate that hair sprays and other consumer products have low volatile organic compounds (VOC's) in the composition. When formulating such a low VOC hair spray, a number of concerns must be addressed. These concerns are intensified as more water is added to the system.

For example, many useful hair fixatives for hair spray compositions are compatible with alcohol or hydrocarbon solvents only. Resin instability, solvent-propellant compatibility, increased viscosity and surface tension, extended dry times, a poor high humidity curl resistance, and negative spray aesthetics, i.e. coarse, wet sprays, poor spray pattern, large particle size and foaming at the actuator, are other problems with low VOC hair spray compositions.

Water also has the tendency to plasticize and soften the film formed by the fixative resin. This has the effect of reducing film stiffness, and, in some cases, has been seen to have a significant negative impact on humidity resistance of the film. Typically, decreased stiffness and humidity resistance are perceived by the consumer as a decrease in set or hold.

Accordingly, there is a need for hydroalcoholic or water-based hair spray fixatives which can be formulated into hair spray compositions which meet current and future VOC regulations.

Preferably, it is desirable to provide such new and effective hair spray polymers or fixatives which can be prepared in hydroalcoholic or water-based hair spray compositions which not only meet VOC requirements, but also exhibit good fixative properties which will meet consumer expectations for stiffness, hold, tack, dry time, particle size, and the like.

The prior art, however, has not particularly been helpful in providing fixatives which satisfy these requirements.

Shih, in U.S. Pat. No. 5,015,708, for example, described a precipitation polymerization process for making terpolymers of (a) a vinyl lactam, e.g. vinyl pyrrolidone; (b) a polymerizable carboxylic acid, e.g. acrylic acid; and (c) a hydrophobic monomer, e.g. lauryl methacrylate, in a predetermined composition, having an actual K-value of 65–80, for use as a thickener, adhesive, dispersant, or in personal care products. None of these compositions, however, have been found to be suitable for use as hair spray fixatives because the terpolymers do not have adequate sprayability. In particular, it has been found that the compositions are quite viscous so that the particles obtained using conventional spray equipment are coarse and have very large particle sizes of greater than 140μ.

Blankenburg, in Ger. Pat. DE 4,223,066 A1, described hair fixative terpolymers of (a) 10–45% of vinyl pyrrolidone, (b) 5–25% of methacrylic acid, and (c) 30–80% of tert-butyl acrylate, n-butyl methacrylate or ethyl methacrylate. However, none of the terpolymers prepared therein included a hydrophobic monomer, which is a desirable associative thickening component in such compositions. The specification merely suggested without further discussion that stearyl acrylate or methacrylate, lauryl methacrylate, ethyl acrylate, n-butyl acrylate or methyl methacrylate could be substituted in part only for component (c).

Accordingly, it is an object of this invention to provide a low VOC hair spray composition having acceptable spray patterns from both pump and aerosol formulations, and advantageous user performance characteristics.

Another object herein is to provide a low VOC hair spray composition including a terpolymer of a vinyl lactam, a polymerizable carboxylic acid and a hydrophobic monomer, in a predetermined compositional range, with a K-value of 30–55, preferably 40–50, which terpolymer provides a fine finishing spray having a particle size of less than 105μ, good hold and stiffness even under high humidity conditions, high curl retention, low initial tack and short drying times, effective combability, superior shine and natural, lusterous appearance on the hair of the user.

SUMMARY OF THE INVENTION

A low VOC (volatile organic compounds) hair spray composition having a combination of desirable spray patterns and user performance characteristics is described herein. The hair fixative resin in such composition is a terpolymer of, by weight, 40–75%, preferably 55–70%, of a vinyl lactam, preferably vinyl pyrrolidone, 15–40%, preferably 18–25%, of a polymerizable carboxylic acid, preferably acrylic acid or methacrylic acid, and 5–25%, preferably 9–20%, of a hydrophobic monomer, preferably a long chain alkyl ($C_8$–$C_{24}$) acrylate, methacrylate, acrylamide or methacrylamide. The terpolymer has a predetermined K-value of 30–55, preferably 40–50 which provides compositions having good sprayability in both pump and aerosol form, and small, fine spray particles.

The terpolymer is present in the hair spray composition in an amount of, by weight, about 2–10%, preferably 3–6%, optionally neutralized with 0–0.25%, preferably 0.05–0.20%, of a neutralizing agent, and including 55% or less of alcohol and water to 100%. Adjuvants, including a corrosion inhibitor, may be included in an amount of up to 5% of the composition.

The hair spray composition of the invention has a suitable viscosity to deliver a fine finishing spray having a particle size of less than 105μ, preferably 40–100μ. The composition provides stiffness and hold under high humidity conditions, exhibits resistance to flaking, desirable combability, has an effective high curl retention characteristic, low initial tack and short drying times and superior hair shine.

DETAILED DESCRIPTION OF THE INVENTION

In accordance with the invention, there is provided herein a low VOC (volatile organic compounds) hair spray composition having a combination of desirable user performance characteristics. The composition includes a hair fixative terpolymer having a predetermined mixture of monomer components and a defined K-value, as follows:

(a) 40–75% by weight, preferably 55–70%, of a vinyl lactam, preferably vinyl pyrrolidone;

(b) 15–40%, preferably 18–25%, of a polymerizable carboxylic acid, preferably acrylic acid or methacrylic acid; and (c) 5–25%, preferably 9–20%, of a hydrophobic monomer, preferably a long chain alkyl ($C_8$–$C_{24}$) acrylate, methacrylate, acrylamide or methacrylamide, and a K-value of 30–55, preferably 40–50.

The low VOC, pump hair spray composition of the invention contains by weight:

(1) the terpolymer, in an amount of 2–10%, preferably 3–6%, optionally including (2) a neutralizing agent, e.g. aminomethyl propanol (AMP), in an amount of 0–0.25%, preferably 0.05–0.20%;

(3) alcohol, preferably ethanol, in an amount of 55% or less, preferably 25–55%, and optionally including one or more of the following;

(4) adjuvants, in an amount of 0–5%, preferably including 0.1–0.6% of a corrosion inhibitor, and (5) water to 100%.

The pump hair spray compositions of the invention can deliver a fine finishing spray from a pump actuator such as the commercial Seaquist Euromist II device having a particle size of less than 105 microns, and usually about 80–90 microns, which particles appear as a fine mist on the hair of the user. For aerosol hair spray compositions, the particle size of the finishing spray is only about 50–80 microns.

The terpolymers of the present invention having the necessary K-value of 30–55, preferably 40–50, are prepared by solution or precipitation polymerization in the presence of a free radical initiator using one or more of the following critical process conditions:

(a) a polymerization temperature of 75°–135° C.;

(b) a large amount of polymerization initiator;

(c) a high temperature free radical initiator; and (d) 1 to 10 wt. % of a chain transfer agent such as isopropanol.

The suitable concentration of lactam monomer (a) in the terpolymer is between about 40–75 wt. %, preferably 55–70%, and of polymerizable carboxylic acid monomer (b) between about 15–40 wt. %, preferably 18–25%. The most preferred monomer (a) is vinyl pyrrolidone and the preferred monomer (b) is acrylic acid.

FUNCTION OF HYDROPHOBIC MONOMER

The long chain alkyl group in the hydrophobic monomer component (C) of the terpolymer provides the low VOC hair spray composition of the present invention with "associative thickener" properties during film formation on the hair of the user. The associative thickening mechanism proceeds as follows. The terpolymer is present in dissolved state in the hydroalcoholic solution with the water soluble lactam monomer in solution and the long chain alkyl groups solvated by the hydroalcoholic solvent. These groups thus are present randomly organized in the solvent. However, upon application of the hair spray upon the hair, the alcohol component of the solvent evaporates rapidly leaving the terpolymer in water alone. The effective concentration of the terpolymer thus is increased beyond its gelation point. Accordingly, the terpolymer is gelled as a rigid fixative film in water which is substantially tack-free. The film then is dried by removal of water from the gel without any noticeable perception of formation of tack. The dry terpolymer film enables the hair to be held firmly to its style for an extended period of time (long term curl retention or hold). Finally, the thus-styled hair may be easily washed or shampooed to remove the fixative film. The associative thickening mechanism is overcome by the surfactants present in the shampoo randomizing the long chain alkyl groups between themselves (associative) and the long alkyl chains of the surfactants, for ease of removal. Surfactants therefor play the same role as ethanol in the 55% VOC formulation as far as randomizing is concerned.

The terpolymer product of this process can be added to a hair spray formulation as a powder or as a 5 to 50 wt. % solids solution or suspension in water, a lower alkanol, cyclohexane, heptane, methylethyl ketone and the like.

Between about 2 and about 10 wt. % terpolymer, more desirably between about 3 and about 6 wt. % terpolymer, is added to an aqueous hair spray solution containing 55 wt. % or less of ethanol.

The formulation may optionally contain one or more nonactive adjuvants in an amount up to about 5 wt. % based on the total composition. Such nonactive additives include a corrosion inhibitor, a surfactant, a film hardening agent, a hair curling agent, a coloring agent, a lustrant, a sequestering agent, a preservative and the like. Typical corrosion inhibitors include methylethyl amine borate, methylisopropyl amine borate, inorganic hydroxides such as ammonium, sodium and potassium hydroxides, nitromethane, dimethyl oxazolidone, 2-dimethylamino-2-methyl-1-propanol, and aminomethyl propanol.

When an aerosol spray is desired, between about 20 and about 45 wt %, preferably between about 30 and about 35 wt. % propellant is included in the basic hair spray formulation. Suitable propellants include di- $C_1$ to $C_3$ alkyl ethers, butane, propane, isopropanol, nitrous oxide, carbon dioxide, difluoroethane, etc. and mixtures thereof. Dimethyl ether is preferred.

The hair sprays of the present invention have a pH of 3–7 and a glass transition temperature (Tg) of 90°–190° C., more desirably a pH of 4–8 and a Tg of from 100° to 170° C.

The invention will now be described more particularly with respect to the following experimental results and working examples.

A. INVENTION EXAMPLES

EXAMPLE 1

Preparation of Terpolymer of K=40*

A 1-liter, 4-neck resin kettle, fitted with an anchor agitator, a nitrogen purge adaptor, a thermometer, two subsurface feeding tubes connected with two feeding pumps, and a reflux condenser, was charged with 192 g. of vinyl pyrrolidone (VP) and 288 g. of ethanol. A nitrogen purge was started and continued throughout the reaction and the reactor content was agitated at about 200 rpm. After about 30 minutes at 65° C., the reactor was charged with 260 microliters of t-butyl peroxy pivalate initiator (Lupersol 11), and then 64 g. of acrylic acid in 96 g. of ethanol and 64 g. of lauryl methacrylate (LM) in 96 g. of ethanol were introduced simultaneously over a period of 3 hours. After one hour the reactor was heated to 78° C. and 100 microliters of Lupersol 11 was added. The reaction proceeded at 78° C. for 2 hours and then another 100 microliters of Lupersol 11 was added. This addition of Lupersol 11 was repeated twice more. After a total reaction time of about 10–11 hours, the reactor was allowed to cool.

*K-value=calculated from relative viscosity of 1% polymer solution using the Fikentscher equation.

The terpolymer obtained had a K-value of 40.

EXAMPLE 2

Preparation of Terpolymer of K=36

A 2-liter, 4-neck resin kettle, fitted with an anchor agitator, a nitrogen purge adaptor, a thermometer, two subsurface feeding tubes connected with two feeding pumps, and a reflux condenser was charged with 50 g. of isopropanol and 950.0 g. of heptane. Nitrogen purging was started and continued throughout the reaction. The solution was heated to 65° C. in 20 minutes and the temperature was held at 65° C. under constant agitation at 200 rpm for 30 minutes. Thereafter 530 microliters of (Lupersol 11) was introduced which was followed by a gradual and simultaneous charge of 150 grams of vinyl pyrrolidone (VP), 50 grams of lauryl methacrylate (LM) and 50 grams of acrylic acid (AA) over a 3 hour period. After an additional hour, the reaction mixture was transferred into a 2-liter stainless steel high pressure reactor containing 2,5-dimethyl-2,5-di(t-butylperoxy) hexane (Lupersol 101) (1.0 grams). The resulting system was purged with nitrogen to 30 psi and vented to 2 psi four times, after which the reactor was held for 8 hours at 130° C. to complete the polymerization. The reactor contents, after cooling to room temperature, were transferred into a flat container and dried in a vacuum oven at 95° C. for 16 hours.

The terpolymer obtained had a K-value of 36.

EXAMPLE 3

Preparation of Terpolymer of K=45

A nitrogen purged, 2-liter, 4-neck resin kettle, fitted with an anchor agitator, a nitrogen purge adaptor, a thermometer, two subsurface feeding tubes connected with two feeding pumps, and a reflux condenser was charged 1,000 grams of heptane under agitation of about 200 rpm while gradually heating to 75° C. After 30 minutes, the reactor was charged with 4.0 g. of Lupersol 11. This was followed by a simultaneous charge of 150 grams of vinyl pyrrolidone (VP), 50 grams of lauryl methacrylate (LM) and 50 grams of acrylic acid (AA) over a 3 hour period. The reaction mixture was held at 75° C. for 1 hour and then transferred into a 2-liter stainless steel high pressure reactor. The high pressure reactor was charged with 1.0 gram of 2,5-dimethyl-2,5-di(t-butylperoxy) hexane initiator (Lupersol 101) and purged with nitrogen to 30 psi and vented to 2 psi. The reaction mixture was then heated to 130° C. and held at that temperature for 8 hours after which the reactor was allowed to cool to room temperature and the contents transferred into flat container where it formed a wet cake. The wet cake was dried in a vacuum oven at 95° C. for 16 hours.

The terpolymer recovered had a K-value of 45.

EXAMPLE 4

Preparation of Terpolymer of K=43

A nitrogen-purged, 2-liter, 4-neck resin kettle, fitted with an anchor agitator, a nitrogen purge adaptor, a thermometer, two subsurface feeding tubes connected with two feeding pumps, and a reflux condenser, was charged with 1,000 g. of heptane while agitating at 200 rpm and gradually heating to 80° C. The solution was held at that temperature for 30 minutes after which 520 microliters of Lupersol 11 was charged and followed by simultaneous charging of 150 g. of vinyl pyrrolidone (VP), 50 g. of acrylic acid (AA), and 50 g. of lauryl methacrylate (LM) over 3 hours at 80° C. After an additional 1 hour, the reaction mixture was transferred into a 2-liter stainless steel high pressure reactor. Then Lupersol 101 (1 g.) was charged to the reactor which had been purged with nitrogen to 30 psi and vented to 2 psi. The reactor was heated to 130° C. and held at that temperature for 8 hours and then allowed to cool to room temperature.

The resulting reaction mixture was transferred into flat container to form a wet cake. The cake was then dried in a vacuum oven at 95° C. for 16 hours.

The terpolymer had a K-value of 43.

EXAMPLE 5

Preparation of Terpolymer of K=39

Example 1 was repeated except that stearyl methacrylate (SM) was substituted for lauryl methacrylate.

The terpolymer had a K-value of 39.

EXAMPLE 6

Preparation of Terpolymer of K=36

A nitrogen purged, 1-liter, 4-neck resin kettle, fitted with an anchor agitator, a nitrogen purge adaptor, a thermometer, two subsurface feeding tubes connected with 3 feeding pumps, a reflux condenser was charged with 480 g. of ethanol while agitating at 200 rpm and heating to 65° C. After 30 minutes, the reactor was charged with 260 microliters of Lupersol 11 followed by a feed of 192 g. of vinyl pyrrolidone, 64 g. of acrylic acid and 64 g. of lauryl methacrylate over a 3 hour period. The reaction was held at 65° C. for an additional hour and then heated to 78° C. after which an additional 100 microliters of Lupersol 11 was added. The reactant mixture was held at 78° C. for 2 hours and the Lupersol 11 addition at 78° C. followed by 2 hour holding was repeated 4 times before cooling and discharging the resulting terpolymer product mixture.

The terpolymer product had a K-value of 36.

TABLE 1

| Invention Ex. No. | Terpolymer (% by wt.) | | | K-Value |
|---|---|---|---|---|
| | VP | AA | LM | |
| 1 | 60 | 20 | 20 | 40 |
| 2 | 68 | 23 | 9 | 36 |
| 3 | 68 | 23 | 9 | 45 |
| 4 | 68 | 23 | 9 | 43 |
| 5 | 68 | 23 | 9* | 39 |
| 6 | 60 | 20 | 20 | 36 |

*stearyl methacrylate (SM)

B. COMPARATIVE EXAMPLES

In order to demonstrate the criticality of a K-value of 30–55, preferably 40–50, in this invention, the following terpolymers having K-values outside this range were prepared using conventional polymerization conditions.

COMPARATIVE EXAMPLE 7

Preparation of Terpolymer K=80

(Example 1 of Shih, U.S. Pat. No. 5,015,708)

A 1-liter, 5-neck reaction kettle was equipped with a condenser, a thermometer, a nitrogen pure tube, two dropping funnels, and a mechanical stirrer. The reactor was precharged with vinyl pyrrolidone (VP) in 500 g. of heptane. The mixture then was heated to 65° C. in nitrogen gas and held for 30 minutes after which t-butylperoxy pivalate (260 microliter) was charged followed by the addition of acrylic acid (AA) and lauryl methacrylate (LM) over a 1 hour period with constant agitation. Additional t-butyl peroxy pivalate (140 microliter) was charged after 2 hours. The reaction mixture then was held at 65° C. for another 2 hours. The mixture was filtered, washed with heptane twice and dried in an oven overnight at 100° C. The white powder obtained then was dried in a vacuum oven at 100° C. overnight.

The terpolymer had a K-value of 80.

COMPARATIVE EXAMPLE 8

Preparation of Terpolymer of K=72

The procedure of Example 7 was repeated to provide a terpolymer having a K-value of 72.

COMPARATIVE EXAMPLE 9

Preparation of Terpolymer of K=65

The procedure of Example 7 was repeated to provide a terpolymer having a K-value of 65.

COMPARATIVE EXAMPLE 10

Preparation of Terpolymer of K=20

A 1-liter, 4-neck resin kettle, fitted with an anchor agitator, a nitrogen purge adaptor, a thermometer, two subsurface feeding tubes connected with two feeding pumps, and a reflux condenser, was charged with 500 g. of isopropanol. A nitrogen purge was started and continued throughout the reaction and the reactor content was agitated at about 200 rpm. After about 30 minutes at 65° C., the reactor was charged with 260 microliters of t-butylperoxy pivalate initiator (Lupersol 11), and then 20 g. of acrylic acid in 20 g. of isopropanol and 60 g. of vinylpyrrolidone, 20 g. of lauryl methacrylate (LM) in 20 g. of isopropanol were introduced simultaneously over a period of 5 hours. The reaction proceeded at 65° C. for 2 hours and then 100 microliters of Lupersol 11 was added. This addition of Lupersol was repeated 3 times. After a total reaction time of about 8 hours, the reactor was allowed to cool.

The terpolymer obtained had a K-value of 20.

Table 2 below summarizes the composition and K-values of the comparative examples.

TABLE 2

| Comparative Ex. No. | Terpolymer (% by wt.) | | | K-Value |
|---|---|---|---|---|
| | VP | AA | LM | |
| 7 | 68 | 23 | 9 | 80 |
| 8 | 68 | 23 | 9 | 72 |
| 9 | 68 | 23 | 9 | 65 |
| 10 | 60 | 20 | 20 | 20 |

Table 3 below summarizes typical low VOC hair spray compositions of the invention.

TABLE 3

| Spray Compositions Components | Pump | | | % by Wt. Aerosol | | |
|---|---|---|---|---|---|---|
| | (A) | (B) | (C) | (A) | (B) | (C) |
| Terpolymer | | | | | | |
| Powder | 4 | — | — | 3 | — | — |
| Soln (40% in EtOH) | — | 10 | — | — | 7.5 | — |
| Soln (20% in EtOH + H$_2$O) | — | — | 20 | — | — | 15 |
| Ethanol (total) | 55 | 49 | 55.0 | 2.0 | 20 | 20 |
| Water (total) | 40.9 | 40.8 | 40.8 | 41.5 | 40.6 | 41.2 |
| Adjuvants | 0.1 | 0.2 | 0.2 | 0.5 | 0.5 | 0.80 |
| Propellant | — | — | — | 35 | 35 | 35 |

Both the invention terpolymers and the comparative terpolymers were evaluated for sprayability and user performance characteristics. The results are shown in Table 4 below.

TABLE 4

Sprayability and User Performance Results for Both Invention and Comparative Examples

| | Invention Ex. No. | | Comparative Ex. No. | | | |
|---|---|---|---|---|---|---|
| | 2 | 3 | 7 | 8 | 9 | 10 |
| K-Value | 36 | 45 | 80 | 72 | 65 | 20 |
| Sprayability | | | | | | |
| Pump | Fine | Fine | Coarse | Coarse | Coarse | Fine |
| Particle size (μ) | 90 | 92 | 159 | 142 | 109 | 75 |
| Aerosol | Fine | Less Fine | Stream | Stream | Stream | Fine |
| Particle size (μ) | 92 | 75 | — | — | — | — |
| Hair Performance | | | | | | |
| High Humidity Curl Retention (HHCR) (%) | | | | | | |
| 90 min. | 95 | 99 | 93 | 91 | 91 | 20 |
| 4 hr. | 86 | 99 | 87 | 85 | 87 | 10 |
| Duration of Tack (sec) | 34 | 30 | 57 | 38 | 37 | 24 |
| Dry Time (sec) | 60 | 50 | 90 | 64 | 77 | 53 |
| Film Hardness | 8 H | 5 H | 8 H | 5 H | 4 H | 9 H |
| Film Stiffness | 6.2 | 8.8 | 7.4 | 6.8 | 7.2 | 4.2 |
| Combability | 5.4 | 4.6 | 6.4 | 4.4 | 6.0 | 6.0 |
| Hair Appearance | Lusterous | Lusterous | Lusterous | Lusterous | Lusterous | Lusterous |

These results demonstrate that invention terpolymers having a predetermined composition with a K-value of 30–55, preferably 40–50, gave excellent spray characteristics, particularly a fine spray and small particle size, from both pump and aerosol formulations, whereas comparative compositions containing a terpolymer having a K-value of 80 provided only coarse particles which were large in size and streamed out of the can rather than forming a desirable fine spray. Terpolymers with a K-value of 20 had good sprayability; however, its high humidity curl retention property decreased to an unacceptable value of 10% compared to 86–99% for the terpolymers of the invention.

The amount of hydrophobic monomer (c) present in the terpolymer of the invention is critical in attaining a clear hair spray composition providing a good stiffness characteristic. More specifically, it has been observed that when the concentration of the hydrophobic monomer exceeds 25 wt. % (e.g. 40 wt. %) of the terpolymer, the resulting terpolymer composition is opaque, before neutralization, and is very cloudy even after neutralization. Upon spraying, it forms films with poor stiffness, 6.6 vs. 8.8 (K=45). Furthermore, less than 5wt. % (e.g. 0%) of the hydrophobic monomer component produces a terpolymer whose composition produces a film which has a stiffness value of only 6.4 vs. 8.8 (K=45).

While the invention has been described with particular reference to certain embodiments thereof, it will be understood that changes and modifications may be made which are within the skill of the art. Accordingly, it is intended to be bound only by the following claims, in which:

What is claimed is:

1. A hair spray composition comprising, by weight,
   (a) about 2–10% of a terpolymer comprising:
      (i) about 60% to about 68% of vinyl pyrrolidone,
      (ii) about 20% to about 23% of acrylic or methacrylic acid, and
      (iii) about 9% to about 20% of lauryl methacrylate or stearyl methacrylate, having a K-value of 36–45,
   (b) 0–0.25% of a neutralizing agent,
   (c) 0–55% of alcohol,
   (d) 0–5% of adjuvants,
   (e) 0–35% of a propellant, and
   (f) water to 100%,
   which composition can deliver a finishing spray having a particle size of less than 105 microns.

2. A hair spray composition according to claim 1 wherein (a) is 3–6%.

3. A hair spray composition according to claim 1 which includes 0.05–0.20% of a neutralizing agent.

4. A hair spray composition according to claim 1 wherein (d) includes corrosion inhibitors.

5. A hair spray composition according to claim 1 which includes 35–55% ethanol.

6. A hair spray composition according to claim 1 which includes 20–35% of a propellant.

7. A hair spray composition according to claim 6 wherein the propellant is dimethyl ether.

* * * * *